United States Patent
Kulick

(10) Patent No.: US 6,494,209 B2
(45) Date of Patent: Dec. 17, 2002

(54) METHOD AND APPARATUS FOR TREATMENT OF SNORING, HYPOPNEA AND APNEA

(76) Inventor: George Kulick, 1208 Walnut St., Freeland, PA (US) 18224

(*) Notice: Subject to any disclaimer, the term of this patent is extended or adjusted under 35 U.S.C. 154(b) by 64 days.

(21) Appl. No.: 09/823,116

(22) Filed: Apr. 2, 2001

(65) Prior Publication Data

US 2002/0139375 A1 Oct. 3, 2002

(51) Int. Cl.[7] ............................................. A61F 5/56
(52) U.S. Cl. ................... 128/848; 128/859; 128/860; 602/902
(58) Field of Search .................... 128/846, 848, 128/859–862, 207.14; 602/902

(56) References Cited

U.S. PATENT DOCUMENTS

| | | | | |
|---|---|---|---|---|
| 2,685,287 A | * | 8/1954 | Golfier | 128/DIG. 20 |
| 3,091,237 A | * | 5/1963 | Skinner | 128/DIG. 20 |
| 4,270,531 A | * | 6/1981 | Blachly | 128/207.14 |
| 5,046,512 A | * | 9/1991 | Murhie | 128/848 |

* cited by examiner

Primary Examiner—Michael A. Brown

(57) ABSTRACT

A one-piece oral device for treatment of obstructive sleep disorders such as snoring hypopnea and apnea comprising a mouthpiece portion that fits within the anterior part of the oral cavity of a person much like the mouthpieces used in snorkel and scuba devices when swimming. The anterior or forward part of the mouthpiece protrudes outwardly through the lips of the user and includes a tongue shaped cavity for receiving the tongue. Bite blocks extending interiorly of the mouthpiece maintain the teeth in spaced-apart relation preventing damage to the tongue. A small channel communicates with the tongue shaped cavity and is connected via a length of tubing to an outside source of low suction pressure for holding the tongue forward.

24 Claims, 2 Drawing Sheets

METHOD AND APPARATUS FOR TREATMENT OF SNORING, HYPOPNEA AND APNEA

BACKGROUND OF THE INVENTION

The disruption of sleep causes excessive sleepiness during the working hours. Sleep research in the past few years suggest that snoring even without sleep apnea syndrome may also disturb sleep significantly. Sleepiness is a global epidemic. Fatigue accounts for about 40 percent of commercial trucking accidents, which causes 4,000 deaths and 12,000 injuries per year. It also causes a breakdown in marital and family ties. The true nature of the challenge, i.e., to identify and treat the millions of people who have sleep apnea syndrome, is truly staggering. Patients with sleep apnea syndrome are in danger of harming themselves and may be at risk to others.

The present invention has been developed to aid in the elimination of snoring and the various degrees of hypopnea and apnea that occur due to pathological disturbances in the sleep process. One of the main reasons of the sleep disturbance is the relaxation of the tongue to varying degrees during the several stages of sleep. When fully awake, the tongue has normal tone as air normally passes in and out of the lungs during respiration. However, during sleep, the tongue is lax. As air is drawn into the lungs by the muscles of respiration, the tongue is drawn back against the posterior wall of the pharynx in a fluttering fashion. As the posterior part of the tongue hits the posterior wall of the pharynx with rapidity, the to and fro action of the tongue causes loud and disturbing snoring sounds. When sleeping in a supine position, the effect of gravity makes the snoring worse.

The more serious type of sleep disturbance is obstructive sleep apnea, which occurs when the tongue goes against the posterior wall of the pharynx preventing any air from entering the lungs. The effort of the muscles of respiration causes the blockage to seal even tighter. The apnea causes a drop in the blood oxygenation and increases the blood carbon dioxide level. The heart is affected adversely with the blood pressure and pulse rate increasing. Sometimes arrhythmias may occur. The brain is affected by the carbon dioxide buildup causing the person to be aroused. On awakening there is a return to tonicity of the muscles of the tongue, which allow normal breathing to resume. After some time the person goes back to sleep and the process occurs all over again.

The American Sleep Apnea Association rates obstructive sleep apnea events per hour as the Respiratory Distress Index (RDI). It rates 0–5 RDI's as normal, 5–20 as mild, 20–40 as moderate, and over 40 as severe. In a few cases RDI's were above 100; with events lasting 90 to 120 seconds with oxygen saturation going below 70% when normal is 95% to 100%. All aspects of quality of life, from physical and emotional health, to social functioning are impaired by the obstructive sleep apnea.

Much research has been done worldwide on correcting sleep disorders. The most prominent treatment used presently is the Mask and Nasal Continuous Positive Airway Pressure (CPAP). The nasal C-PAP is more accepted than the mask but compliance is poor. Frequent side affects occur such as dryness, mucous congestion, sinusitis, rhino rhea, sneezing, and mucous in the throat. Breathing out against positive air pressure is also discomforting. Other treatments include a tongue retaining device (TRD) made of soft plastic that have a tongue shaped cavity that is supposed to hold the tongue in a forward position after a suction is formed within the mouth by the user. The negative pressure created within the mouth draws the tongue forward into the tongue cavity. With this method, adequate suction is not developed and not maintained for long. Another device clamps the tongue and holds it in a forward position. Some units were uncomfortable to wear. In some experiments, it was worn only half of the night. Despite drawbacks, the TRD was found to decrease the number of apnea events by approximately 50%. Thus far, TRD has not excited a lot of enthusiasm in the research community. The Samelson device (U.S. Pat. No. 4,304,227) holds the tongue forward within a cavity with suction created by the tongue forcing its way into the cavity. However, this suction force does not last for a prolonged period of time. The Samelson device also does not allow any mouth breathing and is not successful if there is any type of obstruction in the nasal passages. Dental devices have been devised to advance the mandible, such as disclosed in U.S. Pat. No. 4,715,368 which enhances the space between the posterior tongue surface and the posterior pharyngeal wall. However, problems arise because of dislocation of the temperomandibular joint causing pain in the joints and sometimes in the teeth. Occasionally a permanent mal occlusion develops.

The present invention differs from the Samelson device by creating a suction with an external source and permitting the user to breathe through the mouth. This is important because even when there is normal nasal anatomy, the nasal passages may become congested, especially when infection or allergies are present.

BRIEF SUMMARY OF THE INVENTION

The embodiment of my invention is a one-piece oral device for treatment of obstructive sleep disorders. The invention includes a mouthpiece portion that fits within the anterior part of the oral cavity of a person much like the mouthpieces used in snorkel and scuba devices when swimming. The anterior or forward part of the invention protrudes outwardly through the lips as illustrated in FIG. 1 and includes a tongue shaped cavity for receiving the tongue. A small channel communicates with the tongue shaped cavity and is connected via a length of tubing to an outside source of low suction pressure. There is no difficulty in swallowing saliva with the tongue being in the forward position throughout the night since the tongue is held forward.

It is one object of the present invention to provide a method and apparatus for reducing or eliminating snoring, hypopnea, or apnea by holding the tongue in a forward position in such a way that no portion of the tongue or other oral soft tissue will vibrate during breathing.

It is a further object of the present invention to provide a method and apparatus for reducing or eliminating snoring, hypopnea, or apnea by not only holding the tongue in a forward position but also permit oral breathing through the mouth particularly should nasal congestion occur.

It is a further object of the present invention to provide a device for reducing or eliminating snoring, hypopnea or apnea which is comfortable to use and easy to manufacture.

These and other objects and advantages of the present invention will become clear from the following description of a preferred embodiment of the invention.

BRIEF DESCRIPTION OF THE DRAWING FIGURES

Figure 7:
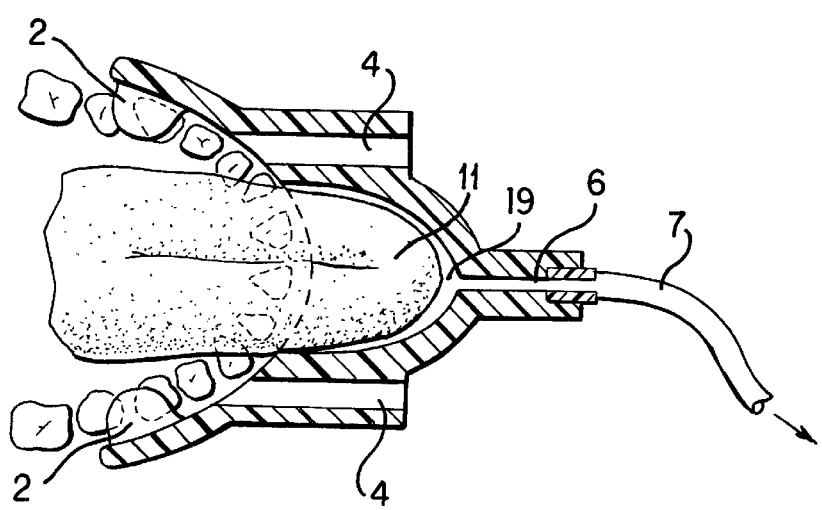

FIG. 7 is a top planar view showing the device held within the oral cavity. The tongue is shown in the forward position. Bite blocks are located near the first molar teeth to limit the closure of the teeth. The oral airway channels are shown to the sides of the tongue cavity.

DETAILED DESCRIPTION OF THE INVENTION

Referring now to the drawings FIGS. 1–7 illustrates the anti-snoring and sleep apnea device in use. Basically the preferred embodiment comprises a mouthpiece 1 held within the oral cavity of a user connected to a suction source 8 via tubing 7. As best seen in FIGS. 2–5 the mouthpiece 1 is preferably molded of any well-known synthetic plastic resin that is pliable yet sufficiently rigid to be self sustaining when held in the mouth. The mouthpiece may be made of any orthodontically acceptable moldable plastic, such as acrylic or other materials within the slate of art. The mouthpiece can also be made of natural rubber wood or metal.

Figure 1:
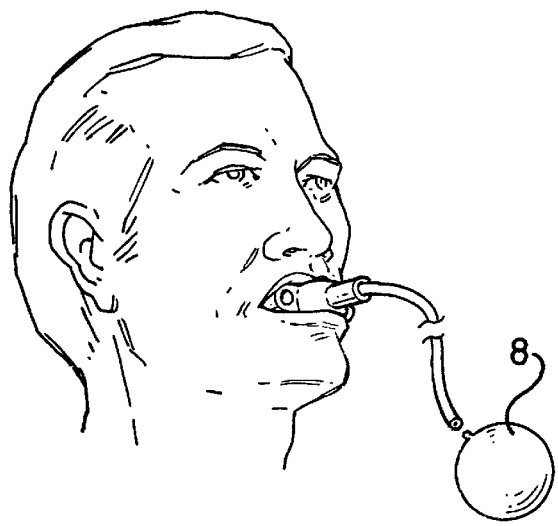
FIG. 1 is a view of device held within the anterior portion of the mouth with an anterior portion of it protruding through the lips.
Figure 2:
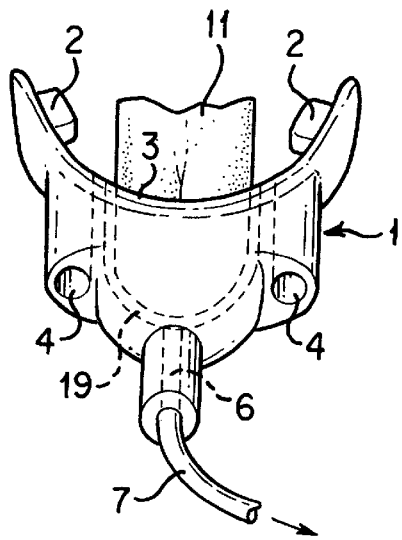
FIG. 2 is a topographic view of the device. Dotted lines depict a tongue shaped cavity two respiration air channels, and a suction channel leading from the tip of the tongue cavity via a length of tubing to an outside source of low suction.
Figure 3:
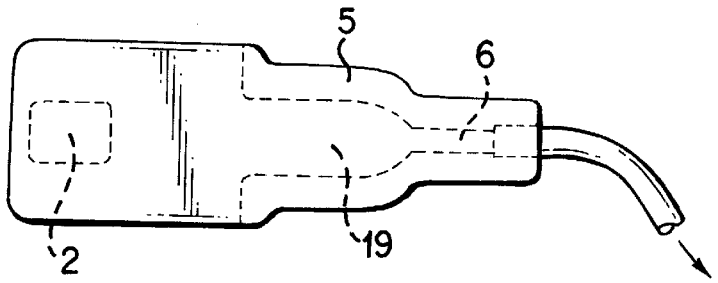
FIG. 3 is a side view of the device. The dotted lines demonstrate the bite block and the tongue shaped cavity with an outlet suction channel at the tip end of device.
Figure 4:
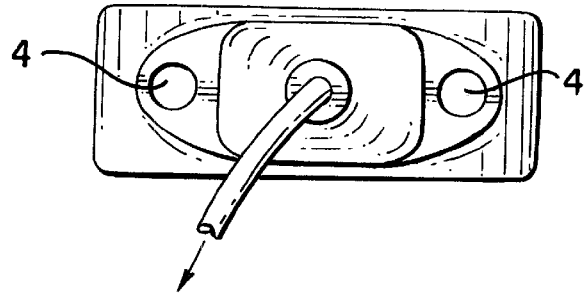
FIG. 4 is a frontal view of the device that shows the entrance of two air channels for oral breathing and the tubing attached to the suction channel.
Figure 5:
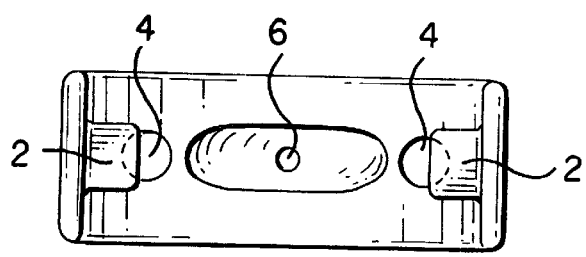
FIG. 5 is a rear view of the device that shows the central tongue cavity with the suction opening at the distal end with the bite blocks and the rear openings of the two air channels.
Figure 6:
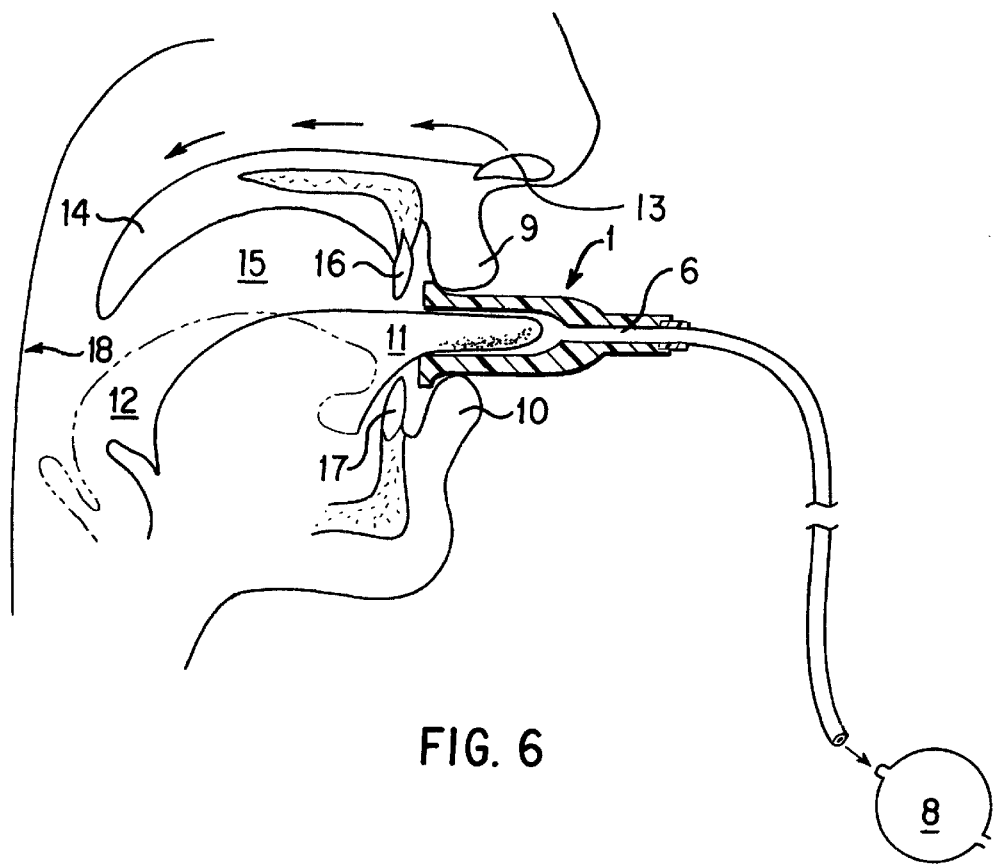
FIG. 6 is a sagittal view of the device within the frontal portion of the mouth and the portion extending out of the mouth. It demonstrates how the tongue is held in a more forward position within the device.

The mouthpiece is comprised of a flange 3 adapted to be positioned between the upper and lower lips and upper and lower teeth of the user as illustrated in FIG. 6. Body portion 5 extends forward of flange 3. A tongue shaped cavity 19 extends through flange 3 into the interior of body portion 5. The tongue shaped cavity 19 is sized and shaped to receive the forward part of the tongue in a snug-like fit. The tongue receiving cavity is positioned between the upper central incisor tooth 16 and the lower central incisor tooth 17, as shown in FIG. 6.

Breathing channels 4 extend through flange 3 and body portion 5 on opposite sides of cavity 19 to permit oral breathing at any time when the device is in use. Bite blocks 2 are formed on opposing sides of flange 3 and extend rearward thereof. Bite blocks 2 are adapted to be held proximately between the upper and lower second bicuspid and/or first molar teeth. The bite blocks are sized to provide sufficient spacing between the teeth to permit the tongue to project forwardly into the tongue-receiving cavity without causing injury to the tongue by the teeth. A suction channel 6 extends from the tongue receive cavity 19 and is connected to a conventional source of suction 8 via tubing 7. Tubing 7 can be connected to suction channel 6 in any conventional manner. Suction force 8 can also be any conventional suction pump such as a MINI-PUMP WITH LONG LIFE MICRO-MO 1624 FAULHABER MOTORS provided by Virtual Industries Inc.

Legend of Numbers Used on the Drawings

1. Mouthpiece
2. Bite blocks adapted to be located proximate the second bicuspid and/or first molar teeth
3. Flange
4. Opening of air passage way into oral cavity
5. Forward extension body portion
6. Suction channel passageway leading out from the tongue cavity
7. Tubing attached to the device for low suction from an outside source
8. Outside source of suction (example: diaphragm electric pump)
9. Upper lip
10. Lower lip
11. Tongue in forward position within device cavity held by light suction
12. Tongue represented by dotted line in normal position within oral cavity
13. Nasal air passageway
14. Uvula of soft palate
15. Oral cavity
16. Upper central incisor tooth
17. Lower central incisor tooth
18. Posterior wall of pharynx
19. Tongue shaped cavity within the device Although the preferred method of manufacturing the present invention is to mold the mouthpiece as a single unitary structure of any suitable synthetic material that displays sufficient rigidity yet pliable properties that would provide comfort and durability for the user, it is within the level of one skilled in the art to make the mouthpiece of rubber, wood or metal or of several separately manufactured parts connected together in a conventional manner. The preferred material for manufacturing the present invention is medical grade silicone rubber.

In use, the device is placed within the mouth and the tongue is inserted into the small tongue-shaped cavity. The low-pressure vacuum unit is then turned on. This keeps the tongue in a forward position throughout the night. The bite blocks limit the closure of the teeth to protect the tongue. The air channels on each side of the tongue cavity provide for easy breathing through the oral airway should any obstruction occur within the nasal passages due to congestion from infections or allergies. Breathing can occur through the Nasal passages or the oral airway or both.

I claim:

1. A device for treating snoring, hypopnea and apnea comprising:

a mouthpiece adapted to be securely retained within the mouth of a user;

said mouthpiece sized and shaped to maintain a user's teeth in spaced apart relation a distance sufficient to permit a user's tongue to extend outwardly of the user's mouth and beyond the user's teeth;

said mouthpiece having a tongue-receiving-cavity therein sized and shaped to smugly receive a forward section of a user's tongue; and said mouthpiece including a suction channel communicating with said tongue-receiving cavity and connected to a suction source;

said mouthpiece having a flange and a pair of bite blocks, each said bite block being attached to and extending inward from an inner surface of said flange.

2. A device as claimed in claim 1, wherein said mouthpiece includes said flange having an inside surface adapted to be positioned adjacent a user's teeth and an outside surface adapted to be positioned adjacent a user's lips, said flange including an opening, said opening defining an entrance into said cavity.

3. A device as claimed in claim 2, wherein said cavity is formed within a forward extension having a hollow interior and extends from said outside surface of said flange, said forward extension being sized and shaped to extend out of the mouth of a user between the user's lips, said cavity defined by said opening and said hollow interior of said extension.

4. A device as claimed in claim 3, further including a plurality of bite blocks extending within said mouthpiece and adapted to maintain said teeth in said spaced apart relationship a sufficient distance to prevent injury to the tongue by the teeth when the device is in use.

5. A device as claimed in claim 4, wherein said suction source includes a vacuum generating means separate from and connected to said suction channel for generating a suction force in said cavity sufficient to hold said forward section of the tongue in said cavity for an extended period of time.

6. A device as claimed in claim 5, wherein said vacuum generating means comprises a suction pump having a suction inlet connected to said cavity by a suction hose.

7. A device as claimed in claim 1, wherein said cavity is formed within a forward extension of said mouthpiece, said forward extension being sized and shaped to extend out of the mouth of a user between the user's lips.

8. A device as claimed in claims 1, further including a plurality of bite blocks extending within said mouthpiece and adapted to maintain said teeth in said spaced apart relationship a sufficient distance to prevent injury to the tongue by the teeth when the device is in use.

9. A device as claimed in claim 1, wherein said suction source includes a vacuum generating means separate from and connected to said suction channel for generating a suction force in said cavity sufficient to hold said forward section of the tongue in said cavity for an extended period of time.

10. A device as claimed in claim 9, wherein said vacuum generating means comprises a suction pump having a suction inlet connected to said cavity by a suction hose.

11. A device for treating snoring, hypopnea and apnea comprising:
   a mouthpiece adapted to be securely retained within the mouth of a user;
   said mouthpiece having a flange and a pair of bite blocks, each said bite block being attached to and extending inward from an inner surface of said flange;
   said mouthpiece sized and shaped to maintain a user's teeth in spaced apart relation a distance sufficient to permit a user's tongue to extend outwardly of the user's mouth and beyond the user's teeth;
   said mouthpiece having a tongue-receiving-cavity therein sized and shaped to snugly receive a forward section of a user's tongue;
   said mouthpiece including a suction channel communicating with said tongue-receiving cavity and adapted to be connected to a suction source; and
   at least one air-breathing passage for providing breathing through the mouth when said device is in use.

12. A device as claimed in claim 11, wherein said mouthpiece includes said flange having an inside surface adapted to be positioned adjacent a user's teeth and an outside surface adapted to be positioned adjacent a user's lips, said flange including an opening, said opening defining an entrance into said cavity.

13. A device as claimed in claim 12, wherein said cavity is formed within a forward extension having a hollow interior and extends from said outside surface of said flange, said forward extension being sized and shaped to extend out of the mouth of a user between the user's lips, said cavity defined by said opening and said hollow interior of said extension, and said at least one air breathing passage comprises an air breathing passage extending along each side of said forward extension and through said flange.

14. A device as claimed in claim 13, further including a plurality of bite blocks extending within said mouthpiece and adapted to maintain said teeth in said spaced apart relationship a sufficient distance to prevent injury to the tongue by the teeth when the device is in use.

15. A device as claimed in claim 14, wherein said air breathing passages are positioned between said bite blocks.

16. A device as claimed in claim 15, and further including a vacuum generating means separate from and connected to said suction channel for generating a suction force in said cavity sufficient to hold said forward section of the tongue in said cavity for an extended period of time.

17. A device as claimed in claim 16, wherein said vacuum generating means comprises a suction pump having a suction inlet connected to said cavity by a suction hose.

18. A device as claimed in any one of claims 1–16, wherein said mouthpiece is made of a synthetic resin, wood, natural rubber or metal.

19. A device as claimed in any one of claims 1–16, wherein said mouthpiece is molded of a medical grade silicone.

20. A device as claimed in claim 11, wherein said cavity is formed within a forward extension of said mouthpiece said forward extension being sized and shaped to extend out of the mouth of a user between the user's lips.

21. A device as claimed in claim 11, further including a plurality of bite blocks extending within said mouthpiece and adapted to maintain said teeth in said spaced apart relationship a sufficient distance to prevent injury to the tongue by the teeth when the device is in use.

22. A device as claimed in claim 11, and further including a vacuum generating means separate from and connected to said suction channel for generating a suction force in said cavity sufficient to hold said forward section of the tongue in said cavity for an extended period of time.

23. A device as claimed in claim 22, wherein said vacuum generating means comprises a suction pump having a suction inlet connected to said cavity by a suction hose.

24. A method for treating snoring, hypopnea and apnea comprising,
   securing a mouthpiece having a tongue receiving cavity in the anterior portion of a
   user's mouth with said tongue receiving cavity positioned between the upper and lower teeth;
   inserting a forward section of said user's tongue into said cavity, holding said tongue within said cavity with a suction force created in said cavity by an external source of negative pressure;
   maintaining said above steps during a period of sleep said mouthpiece having a flange and a pair of bite blocks, each said bite block being attached to and extending inward from an inner surface of said flange.

* * * * *